(12) United States Patent
Waldman

(10) Patent No.: US 7,598,229 B2
(45) Date of Patent: Oct. 6, 2009

(54) METASTATIC COLORECTAL CANCER VACCINE

(75) Inventor: Scott A. Waldman, Ardmore, PA (US)

(73) Assignee: Thomas Jefferson University, Philadelphia, PA (US)

(*) Notice: Subject to any disclaimer, the term of this patent is extended or adjusted under 35 U.S.C. 154(b) by 370 days.

(21) Appl. No.: 10/695,578

(22) Filed: Oct. 27, 2003

(65) Prior Publication Data

US 2004/0141990 A1 Jul. 22, 2004

Related U.S. Application Data

(63) Continuation of application No. 09/180,237, filed as application No. PCT/US97/07565 on May 2, 1997, now abandoned.

(60) Provisional application No. 60/017,018, filed on May 3, 1996.

(51) Int. Cl.
*A01N 43/04* (2006.01)
(52) U.S. Cl. .................................................. 514/44
(58) Field of Classification Search ................ 514/44
See application file for complete search history.

(56) References Cited

U.S. PATENT DOCUMENTS

| | | | |
|---|---|---|---|
| 4,022,878 A | 5/1977 | Gross | 424/1.5 |
| 4,329,281 A | 5/1982 | Christenson et al. | 260/112 B |
| 4,526,716 A | 7/1985 | Stevens | 260/112.5 R |
| 4,736,866 A | 4/1988 | Leder et al. | 800/1 |
| 4,873,191 A | 10/1989 | Wagner et al. | 435/172.3 |
| 4,945,050 A | 7/1990 | Sanford et al. | 435/172.1 |
| 5,017,487 A | 5/1991 | Stunnenberg et al. | 435/172.3 |
| 5,037,645 A | 8/1991 | Strahilevitz | 424/85.8 |
| 5,112,606 A | 5/1992 | Shiosaka et al. | 530/389.2 |
| 5,237,051 A | 8/1993 | Garbers et al. | |
| 5,273,745 A | 12/1993 | Schirrmacher | |
| 5,352,775 A | 10/1994 | Albertsen et al. | 536/23.1 |
| 5,484,596 A | 1/1996 | Hanna et al. | |
| 5,518,888 A | 5/1996 | Waldman | 435/7.23 |
| 5,601,990 A | 2/1997 | Waldman | 435/7.23 |
| 5,731,159 A | 3/1998 | Waldman et al. | 435/7.23 |
| 5,879,656 A | 3/1999 | Waldman et al. | 424/149 |

FOREIGN PATENT DOCUMENTS

| WO | WO 90/11092 | 10/1990 |
|---|---|---|
| WO | WO 95/11694 | 5/1995 |

OTHER PUBLICATIONS

Roitt et al (Immunology, 1993, 3rd ed, Mosby, London).*
Holmes (Exp. Opin. Invest. Drugs, 2001, 10(3):511-519).*
Crystal, R.G. (Science, vol. 270, Oct. 1995, pp. 404-410).*
Tait et al. (Clin.Canc.Res., vol. 5, Jul. 1999, pp. 1708-1714).*
Gura (Science, 1997, 278:1041-1042.).*
Almenoff et al (Journal of Biological Chemistry, 1994, 24(17): 16610-16617).*
Almenoff et al (journal of Biological Chemistry, Jun. 17, 1994, 269(24):16610-16617).*
Verma et al. (Nature 1997, 389: 239-242).*
Amalfitano et al. (Current Gene Therapy 2002, 2: 111-133).*
Almenoff et al., "Induction of heat-stable enterotoxin receptor activity by a human Alu repeat," *J. Biol. Chem.*, 1994, 269(24), 16610-16617.
Berd et al., "Immunization with Haptenized, Autologous Tumor Cells Induces Inflammation of Human Melanoma Metastases", *Cancer Res.*, 1991, 51, 2731-2734.
Berd et al., "Induction of Cell-mediated Immunity to Autologous Melanoma Cells and Regression of Metastases after Treatment with a Melanoma Cell Vaccine Preceded by Cyclophosphamide", *Cancer Res.*, 1986, 46, 2572-2577.
Carrithers et al., "*Escherichia coli* heat-stable toxin receptors in human colonic tumors," *Gastroenterology*, 1994, 107, 1653-1661.
Carrithers et al., "*Escherichia coli* heat-stable enterotoxin receptors. A novel marker for colorectal tumors," *Diseases Colon & Rectum*, 1996, 39(2), 171-181.
Francis et al., Peptide Vaccines Based on Enhanced Immunogenicity of Peptide Epitopes Presented with T-Cell Determinants or Hepatitis B Core Protein, *Methods in Enzymol.*, 1989, 178, 659-676.
MacLean et al., "Immunization of breast cancer patients using a synthetic sialyl-Tn glycoconjugate plus Detox adjuvant", *Cancer Immunol. Immunother.*, 1993, 36, 215-222.
Miller et al., "The Induction of Hapten-Specific T Cell Tolerance by Using Hapten-Modified Lymphoid Cells", *J. Immunol.*, 1976, 117(5:1), 1519-1526.
Rudner et al., "Regulation of cell signaling by the cytoplasmic domains of the healt-stable enterotoxin receptor: Identification of autoinhibitory and activating motifs", *Proc. Natl. Acad. Sci.*, 1995, 92, 5169-5173.
Sad et al., "Bypass of carrier-induced epitope-specific suppression using a T-helper epitope", *Immunology*, 1992, 76, 599-603.
Waldman et al., "Immunoaffinity Purification of Soluble Guanylyl Cyclase", *Methods Enzymol.*, 1991, 195, 391-396.
Banchereau et al., "Immune and clinical responses in patient with metastatic melanoma to CD34+ progenitor-derived dendritic cell vaccine," *Cancer Research* (2001) 61:6451-6458.
Bellone et al., "Cancer immunotherapy: synthetic and natural peptides in the balance," *Immunology Today* (1999) 20(10):457-462.
Carrithers et al., "*Escherichia coli* heat-stable toxin receptors in human colonic tumors," *Gastroenterology* (1994) 107:1653-1661.
Celis et al., "Identification of potential CTL epitopes of tumor-associated antigen MAGE-1 for five common HLA-A alleles," *Molecular Immunology* (1994) 31(18):1423-1430.
Disis et al., "Peptide-based, but not whole protein, vaccines elicit immunity to HER-2/neu, oncogenic self-protein," *J. of Immunology* (1996) 156:3151-3158.

(Continued)

*Primary Examiner*—Sean E Aeder
(74) *Attorney, Agent, or Firm*—Pepper Hmailton LLP

(57) ABSTRACT

The invention relates to prophylactic and therapeutic vaccines for protecting individuals against metastatic colorectal cancer and for treating individuals who are suffering from metastatic colorectal cancer.

9 Claims, No Drawings

OTHER PUBLICATIONS

Foon et al., "Clinical and immune responses in resected colon cancer patients treated with anti-idiotype monoclonal antibody vaccine that mimics the carcinoembryonic antigen," *Journal of Clinical Oncology* (1999) 17(9):2889-2895.

Herbert et al., *The Dictionary of Immunology*, Academic Press, 4th ed. (1995).

Greenspan et al., "Defining epitopes: It's not as easy as it seems," *Nature Biotechnology* (1999) 7:936-937.

Gura "Systems for identifying new drugs are often faulty," *Science* (1997) 278:1041-1042.

Mallo et al., "Expression of the *Cdx1* and *Cdx2* homeotic genes leads to reduced malignancy in colon cancer-derived cells," *J. Biological Chemistry* (1998) 273(22):14030-14036.

Nelson et al., *J. Nat'l. Can. Ins.* (1996) 88(8):468-488.

Reynolds et al., "Vaccine-induced CD8+ T-cell responses to MAGE-3 correlate with clinical outcome in patients with melanoma," *Clinical Cancer Research* (2003)9:657-662.

Singh et al., "Isolation and expression of a guanylate cyclase-coupled heat stable enterotoxin receptor cDNA from a human colonic cell line," *Biochem. Biophy. Res. Comm.* (1991) 179(3):1455-1463.

Smith "Cancer and the immune system," *Pediatr Clin North Am.* (1994) 41(4) 841-850.

Spitler "Cancer vaccines: the interferon analogy," *Cancer Biotherapy* (1995) 10:1-3.

Welzien HU "Renaissance for hapten-specific T lymphocytes: implications for basic and applied research," *Z Naturforsch [C]* (1992) 47(5-6):323-328.

Miller et al., "Improved survival of patients with Melanoma with an antibody response to immunization of a polyvalent melanoma vaccine," *Cancer* (1995) 75(2):495-502.

* cited by examiner

SEQUENCE LISTING

```
<160> NUMBER OF SEQ ID NOS: 2

<210> SEQ ID NO 1
<211> LENGTH: 3786
<212> TYPE: DNA
<213> ORGANISM: Homo sapiens
<220> FEATURE:
<221> NAME/KEY: CDS
<222> LOCATION: (118)..(3336)

<400> SEQUENCE: 1
tggagtgggc tgagggactc cactagaggc tgtccatctg gattccctgc ctccctagga     60
gcccaacaga gcaaagcaag tgggcacaag gagtatggtt ctaacgtgat tggggtc       117
y
atg aag acg ttg ctg ttg gac ttg gct ttg tgg tca ctg ctc ttc cag      165
Met Lys Thr Leu Leu Leu Asp Leu Ala Leu Trp Ser Leu Leu Phe Gln
  1               5                  10                  15
y
ccc ggg tgg ctg tcc ttt agt tcc cag gtg agt cag aac tgc cac aat      213
Pro Gly Trp Leu Ser Phe Ser Ser Gln Val Ser Gln Asn Cys His Asn
             20                  25                  30
y
ggc agc tat gaa atc agc gtc ctg atg atg ggc aac tca gcc ttt gca      261
Gly Ser Tyr Glu Ile Ser Val Leu Met Met Gly Asn Ser Ala Phe Ala
         35                  40                  45
y
gag ccc ctg aaa aac ttg gaa gat gcg gtg aat gag ggg ctg gaa ata      309
Glu Pro Leu Lys Asn Leu Glu Asp Ala Val Asn Glu Gly Leu Glu Ile
     50                  55                  60
y
gtg aga gga cgt ctg caa aat gct ggc cta aat gtg act gtg aac gct      357
Val Arg Gly Arg Leu Gln Asn Ala Gly Leu Asn Val Thr Val Asn Ala
 65                  70                  75                  80
y
act ttc atg tat tcg gat ggt ctg att cat aac tca ggc gac tgc cgg      405
Thr Phe Met Tyr Ser Asp Gly Leu Ile His Asn Ser Gly Asp Cys Arg
                 85                  90                  95
y
agt agc acc tgt gaa ggc ctc gac cta ctc agg aaa att tca aat gca      453
Ser Ser Thr Cys Glu Gly Leu Asp Leu Leu Arg Lys Ile Ser Asn Ala
            100                 105                 110
y
caa cgg atg ggc tgt gtc ctc ata ggg ccc tca tgt aca tac tcc acc      501
Gln Arg Met Gly Cys Val Leu Ile Gly Pro Ser Cys Thr Tyr Ser Thr
        115                 120                 125
```

-continued

| | | | | | | | | | | | | | | | | |
|---|---|---|---|---|---|---|---|---|---|---|---|---|---|---|---|---|
| y ttc | cag | atg | tac | ctt | gac | aca | gaa | ttg | agc | tac | ccc | atg | atc | tca | gct | 549 |
| Phe | Gln | Met | Tyr | Leu | Asp | Thr | Glu | Leu | Ser | Tyr | Pro | Met | Ile | Ser | Ala | |
| 130 | | | | | 135 | | | | | 140 | | | | | | |
| y gga | agt | ttt | gga | ttg | tca | tgt | gac | tat | aaa | gaa | acc | tta | acc | agg | ctg | 597 |
| Gly | Ser | Phe | Gly | Leu | Ser | Cys | Asp | Tyr | Lys | Glu | Thr | Leu | Thr | Arg | Leu | |
| 145 | | | | 150 | | | | | 155 | | | | | 160 | | |
| y atg | tct | cca | gct | aga | aag | ttg | atg | tac | ttc | ttg | gtt | aac | ttt | tgg | aaa | 645 |
| Met | Ser | Pro | Ala | Arg | Lys | Leu | Met | Tyr | Phe | Leu | Val | Asn | Phe | Trp | Lys | |
| | | | 165 | | | | | 170 | | | | | 175 | | | |
| y acc | aac | gat | ctg | ccc | ttc | aaa | act | tat | tcc | tgg | agc | act | tcg | tat | gtt | 693 |
| Thr | Asn | Asp | Leu | Pro | Phe | Lys | Thr | Tyr | Ser | Trp | Ser | Thr | Ser | Tyr | Val | |
| | | 180 | | | | | 185 | | | | | 190 | | | | |
| y tac | aag | aat | ggt | aca | gaa | act | gag | gac | tgt | ttc | tgg | tac | ctt | aat | gct | 741 |
| Tyr | Lys | Asn | Gly | Thr | Glu | Thr | Glu | Asp | Cys | Phe | Trp | Tyr | Leu | Asn | Ala | |
| | 195 | | | | | 200 | | | | | 205 | | | | | |
| y ctg | gag | gct | agc | gtt | tcc | tat | ttc | tcc | cac | gaa | ctc | ggc | ttt | aag | gtg | 789 |
| Leu | Glu | Ala | Ser | Val | Ser | Tyr | Phe | Ser | His | Glu | Leu | Gly | Phe | Lys | Val | |
| 210 | | | | | 215 | | | | | 220 | | | | | | |
| y gtg | tta | aga | caa | gat | aag | gag | ttt | cag | gat | atc | tta | atg | gac | cac | aac | 837 |
| Val | Leu | Arg | Gln | Asp | Lys | Glu | Phe | Gln | Asp | Ile | Leu | Met | Asp | His | Asn | |
| 225 | | | | 230 | | | | | 235 | | | | | 240 | | |
| y agg | aaa | agc | aat | gtg | att | att | atg | tgt | ggt | ggt | cca | gag | ttc | ctc | tac | 885 |
| Arg | Lys | Ser | Asn | Val | Ile | Ile | Met | Cys | Gly | Gly | Pro | Glu | Phe | Leu | Tyr | |
| | | | 245 | | | | | 250 | | | | | 255 | | | |
| y aag | ctg | aag | ggt | gac | cga | gca | gtg | gct | gaa | gac | att | gtc | att | att | cta | 933 |
| Lys | Leu | Lys | Gly | Asp | Arg | Ala | Val | Ala | Glu | Asp | Ile | Val | Ile | Ile | Leu | |
| | | 260 | | | | | 265 | | | | | 270 | | | | |
| y gtg | gat | ctt | ttc | aat | gac | cag | tac | ttg | gag | gac | aat | gtc | aca | gcc | cct | 981 |
| Val | Asp | Leu | Phe | Asn | Asp | Gln | Tyr | Leu | Glu | Asp | Asn | Val | Thr | Ala | Pro | |
| | 275 | | | | | 280 | | | | | 285 | | | | | |
| gac | tat | atg | aaa | aat | gtc | ctt | gtt | ctg | acg | ctg | tct | cct | ggg | aat | tcc | 1029 |
| Asp | Tyr | Met | Lys | Asn | Val | Leu | Val | Leu | Thr | Leu | Ser | Pro | Gly | Asn | Ser | |
| 290 | | | | | 295 | | | | | 300 | | | | | | |
| ctt | cta | aat | agc | tct | ttc | tcc | agg | aat | cta | tca | cca | aca | aaa | cga | gac | 1077 |
| Leu | Leu | Asn | Ser | Ser | Phe | Ser | Arg | Asn | Leu | Ser | Pro | Thr | Lys | Arg | Asp | |
| 305 | | | | 310 | | | | | 315 | | | | | 320 | | |
| ttt | cgt | ctt | gcc | tat | ttg | aat | gga | atc | ctc | gtc | ttt | gga | cat | atg | ctg | 1125 |
| Phe | Arg | Leu | Ala | Tyr | Leu | Asn | Gly | Ile | Leu | Val | Phe | Gly | His | Met | Leu | |
| | | | 325 | | | | | 330 | | | | | 335 | | | |
| aag | ata | ttt | ctt | gaa | aat | gga | gaa | aat | att | acc | acc | ccc | aaa | ttt | gct | 1173 |
| Lys | Ile | Phe | Leu | Glu | Asn | Gly | Glu | Asn | Ile | Thr | Thr | Pro | Lys | Phe | Ala | |
| | | | 340 | | | | | 345 | | | | | 350 | | | |
| cat | gcc | ttc | agg | aat | ctc | act | ttt | gaa | ggg | tat | gac | ggt | cca | gtg | acc | 1221 |
| His | Ala | Phe | Arg | Asn | Leu | Thr | Phe | Glu | Gly | Tyr | Asp | Gly | Pro | Val | Thr | |
| | | 355 | | | | | 360 | | | | | 365 | | | | |
| ttg | gat | gac | tgg | ggg | gat | gtt | gac | agt | acc | atg | gtg | ctt | ctg | tat | acc | 1269 |
| Leu | Asp | Asp | Trp | Gly | Asp | Val | Asp | Ser | Thr | Met | Val | Leu | Leu | Tyr | Thr | |
| | 370 | | | | | 375 | | | | | 380 | | | | | |
| tct | gtg | gac | acc | aag | aaa | tac | aag | gtt | ctt | ttg | acc | tat | gat | acc | cac | 1317 |
| Ser | Val | Asp | Thr | Lys | Lys | Tyr | Lys | Val | Leu | Leu | Thr | Tyr | Asp | Thr | His | |
| 385 | | | | | 390 | | | | | 395 | | | | | 400 | |
| gta | aat | aag | acc | tat | cct | gtg | gat | atg | agc | ccc | aca | ttc | act | tgg | aag | 1365 |
| Val | Asn | Lys | Thr | Tyr | Pro | Val | Asp | Met | Ser | Pro | Thr | Phe | Thr | Trp | Lys | |
| | | | 405 | | | | | 410 | | | | | 415 | | | |
| aac | tct | aaa | ctt | cct | aat | gat | att | aca | ggc | cgg | ggc | cct | cag | atc | ctg | 1413 |
| Asn | Ser | Lys | Leu | Pro | Asn | Asp | Ile | Thr | Gly | Arg | Gly | Pro | Gln | Ile | Leu | |
| | | | 420 | | | | | 425 | | | | | 430 | | | |
| atg | att | gca | gtc | ttc | acc | ctc | act | gga | gct | gtg | gtg | ctg | ctc | ctg | ctc | 1461 |
| Met | Ile | Ala | Val | Phe | Thr | Leu | Thr | Gly | Ala | Val | Val | Leu | Leu | Leu | Leu | |

```
                435                 440                 445
gtc gct ctc ctg atg ctc aga aaa tat aga aaa gat tat gaa ctt cgt      1509
Val Ala Leu Leu Met Leu Arg Lys Tyr Arg Lys Asp Tyr Glu Leu Arg
    450                 455                 460 cag aaa aaa tgg tcc cac att cct cct gaa aat atc ttt cct ctg gag      1557
Gln Lys Lys Trp Ser His Ile Pro Pro Glu Asn Ile Phe Pro Leu Glu
465                 470                 475                 480 acc aat gag acc aat cat gtt agc ctc aag atc gat gat gac aaa aga      1605
Thr Asn Glu Thr Asn His Val Ser Leu Lys Ile Asp Asp Asp Lys Arg
            485                 490                 495 cga gat aca atc cag aga cta cga cag tgc aaa tac gtc aaa aag cga      1653
Arg Asp Thr Ile Gln Arg Leu Arg Gln Cys Lys Tyr Val Lys Lys Arg
        500                 505                 510 gtg att ctc aaa gat ctc aag cac aat gat ggt aat ttc act gaa aaa      1701
Val Ile Leu Lys Asp Leu Lys His Asn Asp Gly Asn Phe Thr Glu Lys
    515                 520                 525 cag aag ata gaa ttg aac aag ttg ctt cag att gac tat tac acc cta      1749
Gln Lys Ile Glu Leu Asn Lys Leu Leu Gln Ile Asp Tyr Tyr Thr Leu
530                 535                 540 acc aag ttc tac ggg aca gtg aaa ctg gat acc atg atc ttc ggg gtg      1797
Thr Lys Phe Tyr Gly Thr Val Lys Leu Asp Thr Met Ile Phe Gly Val
545                 550                 555                 560 ata gaa tac tgt gag aga gga tcc ctc cgg gaa gtt tta aat gac aca      1845
Ile Glu Tyr Cys Glu Arg Gly Ser Leu Arg Glu Val Leu Asn Asp Thr
            565                 570                 575 att tcc tac cct gat ggc aca ttc atg gat tgg gag ttt aag atc tct      1893
Ile Ser Tyr Pro Asp Gly Thr Phe Met Asp Trp Glu Phe Lys Ile Ser
        580                 585                 590 gtc ttg tat gac att gct aag gga atg tca tat ctg cac tcc agt aag      1941
Val Leu Tyr Asp Ile Ala Lys Gly Met Ser Tyr Leu His Ser Ser Lys
    595                 600                 605 aca gaa gtc cat ggt cgt ctg aaa tct acc aac tgc gta gtg gac agt      1989
Thr Glu Val His Gly Arg Leu Lys Ser Thr Asn Cys Val Val Asp Ser
610                 615                 620 aga atg gtg gtg aag atc act gat ttt ggc tgc aat tcc att ttg cct      2037
Arg Met Val Val Lys Ile Thr Asp Phe Gly Cys Asn Ser Ile Leu Pro
625                 630                 635                 640 cca aaa aag gac ctg tgg aca gct cca gag cac ctc cgc caa gcc aac      2085
Pro Lys Lys Asp Leu Trp Thr Ala Pro Glu His Leu Arg Gln Ala Asn
            645                 650                 655 atc tct cag aaa gga gat gtg tac agc tat ggg atc atc gca cag gag      2133
Ile Ser Gln Lys Gly Asp Val Tyr Ser Tyr Gly Ile Ile Ala Gln Glu
        660                 665                 670 atc att ctg cgg aaa gaa acc ttc tac act ttg agc tgt cgg gac cgg      2181
Ile Ile Leu Arg Lys Glu Thr Phe Tyr Thr Leu Ser Cys Arg Asp Arg
    675                 680                 685 aat gag aag att ttc aga gtg gaa aat tcc aat gga atg aaa ccc ttc      2229
Asn Glu Lys Ile Phe Arg Val Glu Asn Ser Asn Gly Met Lys Pro Phe
690                 695                 700 cgc cca gat tta ttc ttg gaa aca gca gag gaa aaa gag cta gaa gtg      2277
Arg Pro Asp Leu Phe Leu Glu Thr Ala Glu Glu Lys Glu Leu Glu Val
705                 710                 715                 720 tac cta ctt gta aaa aac tgt tgg gag gaa gat cca gaa aag aga cca      2325
Tyr Leu Leu Val Lys Asn Cys Trp Glu Glu Asp Pro Glu Lys Arg Pro
            725                 730                 735 gat ttc aaa aaa att gag act aca ctt gcc aag ata ttt gga ctt ttt      2373
Asp Phe Lys Lys Ile Glu Thr Thr Leu Ala Lys Ile Phe Gly Leu Phe
        740                 745                 750 cat gac caa aaa aat gaa agc tat atg gat acc ttg atc cga cgt cta      2421
```

-continued

```
                His Asp Gln Lys Asn Glu Ser Tyr Met Asp Thr Leu Ile Arg Arg Leu
                        755                 760                 765 cag cta tat tct cga aac ctg gaa cat ctg gta gag gaa agg aca cag         2469
Gln Leu Tyr Ser Arg Asn Leu Glu His Leu Val Glu Glu Arg Thr Gln
770                 775                 780 ctg tac aag gca gag agg gac agg gct gac aga ctt aac ttt atg ttg         2517
Leu Tyr Lys Ala Glu Arg Asp Arg Ala Asp Arg Leu Asn Phe Met Leu
785                 790                 795                 800 ctt cca agg cta gtg gta aag tct ctg aag gag aaa ggc ttt gtg gag         2565
Leu Pro Arg Leu Val Val Lys Ser Leu Lys Glu Lys Gly Phe Val Glu
                805                 810                 815 ccg gaa cta tat gag gaa gtt aca atc tac ttc agt gac att gta ggt         2613
Pro Glu Leu Tyr Glu Glu Val Thr Ile Tyr Phe Ser Asp Ile Val Gly
                820                 825                 830 ttc act act atc tgc aaa tac agc acc ccc atg gaa gtg gtg gac atg         2661
Phe Thr Thr Ile Cys Lys Tyr Ser Thr Pro Met Glu Val Val Asp Met
                835                 840                 845 ctt aat gac atc tat aag agt ttt gac cac att gtt gat cat cat gat         2709
Leu Asn Asp Ile Tyr Lys Ser Phe Asp His Ile Val Asp His His Asp
850                 855                 860 gtc tac aag gtg gaa acc atc ggt gat gcg tac atg gtg gct agt ggt         2757
Val Tyr Lys Val Glu Thr Ile Gly Asp Ala Tyr Met Val Ala Ser Gly
865                 870                 875                 880 ttg cct aag aga aat ggc aat cgg cat gca ata gac att gcc aag atg         2805
Leu Pro Lys Arg Asn Gly Asn Arg His Ala Ile Asp Ile Ala Lys Met
                885                 890                 895 gcc ttg gaa atc ctc agc ttc atg ggg acc ttt gag ctg gag cat ctt         2853
Ala Leu Glu Ile Leu Ser Phe Met Gly Thr Phe Glu Leu Glu His Leu
                900                 905                 910 cct ggc ctc cca ata tgg att cgc att gga gtt cac tct ggt ccc tgt         2901
Pro Gly Leu Pro Ile Trp Ile Arg Ile Gly Val His Ser Gly Pro Cys
                915                 920                 925 gct gct gga gtt gtg gga atc aag atg cct cgt tat tgt cta ttt gga         2949
Ala Ala Gly Val Val Gly Ile Lys Met Pro Arg Tyr Cys Leu Phe Gly
                930                 935                 940 gat acg gtc aac aca gcc tct agg atg gaa tcc act ggc ctc cct ttg         2997
Asp Thr Val Asn Thr Ala Ser Arg Met Glu Ser Thr Gly Leu Pro Leu
945                 950                 955                 960 aga att cac gtg agt ggc tcc acc ata gcc atc ctg aag aga act gag         3045
Arg Ile His Val Ser Gly Ser Thr Ile Ala Ile Leu Lys Arg Thr Glu
                965                 970                 975 tgc cag ttc ctt tat gaa gtg aga gga gaa aca tac tta aag gga aga         3093
Cys Gln Phe Leu Tyr Glu Val Arg Gly Glu Thr Tyr Leu Lys Gly Arg
                980                 985                 990 gga aat gag act acc tac tgg ctg act ggg atg aag gac cag aaa ttc         3141
Gly Asn Glu Thr Thr Tyr Trp Leu Thr Gly Met Lys Asp Gln Lys Phe
                995                 1000                1005 aac ctg cca acc cct cct act gtg gag aat caa cag cgt ttg caa gca         3189
Asn Leu Pro Thr Pro Pro Thr Val Glu Asn Gln Gln Arg Leu Gln Ala
        1010                1015                1020 gaa ttt tca gac atg att gcc aac tct tta cag aaa aga cag gca gca         3237
Glu Phe Ser Asp Met Ile Ala Asn Ser Leu Gln Lys Arg Gln Ala Ala
1025                1030                1035                1040 ggg ata aga agc caa aaa ccc aga cgg gta gcc agc tat aaa aaa ggc         3285
Gly Ile Arg Ser Gln Lys Pro Arg Arg Val Ala Ser Tyr Lys Lys Gly
                1045                1050                1055 act ctg gaa tac ttg cag ctg aat acc aca gac aag gag agc acc tat         3333
Thr Leu Glu Tyr Leu Gln Leu Asn Thr Thr Asp Lys Glu Ser Thr Tyr
            1060                1065                1070
```

```
ttt taaacctaaa tgaggtataa ggactcacac aaattaaaat acagctgcac    3386
Phe tgaggccagg caccctcagg tgtcctgaaa gcttactttc ctgagacctc atgaggcaga    3446
aatgtcttag gcttggctgc cctgtttgga ccatggactt tctttgcatg aatcagatgt    3506
gttctcagtg aaataactac cttccactct ggaaccttat tccagcagtt gttccaggga    3566
gcttctacct ggaaaagaaa agaatttcat ttattttttg tttgtttatt tttatcgttt    3626
ttgtttactg gctttccttc tgtattcata agattttta aattgtcata attatatttt    3686
aaatacccat cttcattaaa gtatatttaa ctcataattt ttgcagaaaa tatgctatat    3746
attaggcaag aataaaagct aaaggtttcc caaaaaaaa                          3786
```

<210> SEQ ID NO 2
<211> LENGTH: 1073
<212> TYPE: PRT
<213> ORGANISM: Homo sapiens

<400> SEQUENCE: 2

```
Met Lys Thr Leu Leu Asp Leu Ala Leu Trp Ser Leu Leu Phe Gln
  1               5                  10                  15

Pro Gly Trp Leu Ser Phe Ser Ser Gln Val Ser Gln Asn Cys His Asn
                 20                  25                  30

Gly Ser Tyr Glu Ile Ser Val Leu Met Met Gly Asn Ser Ala Phe Ala
             35                  40                  45

Glu Pro Leu Lys Asn Leu Glu Asp Ala Val Asn Glu Gly Leu Glu Ile
         50                  55                  60

Val Arg Gly Arg Leu Gln Asn Ala Gly Leu Asn Val Thr Val Asn Ala
 65                  70                  75                  80

Thr Phe Met Tyr Ser Asp Gly Leu Ile His Asn Ser Gly Asp Cys Arg
                 85                  90                  95

Ser Ser Thr Cys Glu Gly Leu Asp Leu Leu Arg Lys Ile Ser Asn Ala
                100                 105                 110

Gln Arg Met Gly Cys Val Leu Ile Gly Pro Ser Cys Thr Tyr Ser Thr
            115                 120                 125

Phe Gln Met Tyr Leu Asp Thr Glu Leu Ser Tyr Pro Met Ile Ser Ala
        130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Leu Glu Asp Asn Val Thr Ala Pro
        275                 280                 285
```

-continued

```
Asp Tyr Met Lys Asn Val Leu Val Leu Thr Leu Ser Pro Gly Asn Ser
290                 295                 300

Leu Leu Asn Ser Ser Phe Ser Arg Asn Leu Ser Pro Thr Lys Arg Asp
305                 310                 315                 320

Phe Arg Leu Ala Tyr Leu Asn Gly Ile Leu Val Phe Gly His Met Leu
                325                 330                 335

Lys Ile Phe Leu Glu Asn Gly Glu Asn Ile Thr Thr Pro Lys Phe Ala
                340                 345                 350

His Ala Phe Arg Asn Leu Thr Phe Glu Gly Tyr Asp Gly Pro Val Thr
                355                 360                 365

Leu Asp Asp Trp Gly Asp Val Asp Ser Thr Met Val Leu Leu Tyr Thr
370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Gln Ile Leu
                420                 425                 430

Met Ile Ala Val Phe Thr Leu Thr Gly Ala Val Val Leu Leu Leu Leu
                435                 440                 445

Val Ala Leu Leu Met Leu Arg Lys Tyr Arg Lys Asp Tyr Glu Leu Arg
450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
                485                 490                 495

Arg Asp Thr Ile Gln Arg Leu Arg Gln Cys Lys Tyr Val Lys Lys Arg
                500                 505                 510

Val Ile Leu Lys Asp Leu Lys His Asn Asp Gly Asn Phe Thr Glu Lys
                515                 520                 525

Gln Lys Ile Glu Leu Asn Lys Leu Leu Gln Ile Asp Tyr Tyr Thr Leu
530                 535                 540

Thr Lys Phe Tyr Gly Thr Val Lys Leu Asp Thr Met Ile Phe Gly Val
545                 550                 555                 560

Ile Glu Tyr Cys Glu Arg Gly Ser Leu Arg Glu Val Leu Asn Asp Thr
                565                 570                 575

Ile Ser Tyr Pro Asp Gly Thr Phe Met Asp Trp Glu Phe Lys Ile Ser
                580                 585                 590

Val Leu Tyr Asp Ile Ala Lys Gly Met Ser Tyr Leu His Ser Ser Lys
                595                 600                 605

Thr Glu Val His Gly Arg Leu Lys Ser Thr Asn Cys Val Val Asp Ser
610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
                645                 650                 655

Ile Ser Gln Lys Gly Asp Val Tyr Ser Tyr Gly Ile Ile Ala Gln Glu
                660                 665                 670

Ile Ile Leu Arg Lys Glu Thr Phe Tyr Thr Leu Ser Cys Arg Asp Arg
                675                 680                 685

Asn Glu Lys Ile Phe Arg Val Glu Asn Ser Asn Gly Met Lys Pro Phe
690                 695                 700
```

-continued

```
Arg Pro Asp Leu Phe Leu Glu Thr Ala Glu Glu Lys Glu Leu Glu Val
705                 710                 715                 720

Tyr Leu Leu Val Lys Asn Cys Trp Glu Glu Asp Pro Glu Lys Arg Pro
                725                 730                 735

Asp Phe Lys Lys Ile Glu Thr Thr Leu Ala Lys Ile Phe Gly Leu Phe
                740                 745                 750

His Asp Gln Lys Asn Glu Ser Tyr Met Asp Thr Leu Ile Arg Arg Leu
                755                 760                 765

Gln Leu Tyr Ser Arg Asn Leu Glu His Leu Val Glu Glu Arg Thr Gln
        770                 775                 780

Leu Tyr Lys Ala Glu Arg Asp Arg Ala Asp Arg Leu Asn Phe Met Leu
785                 790                 795                 800

Leu Pro Arg Leu Val Lys Ser Leu Lys Glu Lys Gly Phe Val Glu
                805                 810                 815

Pro Glu Leu Tyr Glu Glu Val Thr Ile Tyr Phe Ser Asp Ile Val Gly
                820                 825                 830

Phe Thr Thr Ile Cys Lys Tyr Ser Thr Pro Met Glu Val Val Asp Met
        835                 840                 845

Leu Asn Asp Ile Tyr Lys Ser Phe Asp His Ile Val Asp His His Asp
    850                 855                 860

Val Tyr Lys Val Glu Thr Ile Gly Asp Ala Tyr Met Val Ala Ser Gly
865                 870                 875                 880

Leu Pro Lys Arg Asn Gly Asn Arg His Ala Ile Asp Ile Ala Lys Met
                885                 890                 895

Ala Leu Glu Ile Leu Ser Phe Met Gly Thr Phe Glu Leu Glu His Leu
                900                 905                 910

Pro Gly Leu Pro Ile Trp Ile Arg Ile Gly Val His Ser Gly Pro Cys
        915                 920                 925

Ala Ala Gly Val Val Gly Ile Lys Met Pro Arg Tyr Cys Leu Phe Gly
        930                 935                 940

Asp Thr Val Asn Thr Ala Ser Arg Met Glu Ser Thr Gly Leu Pro Leu
945                 950                 955                 960

Arg Ile His Val Ser Gly Ser Thr Ile Ala Ile Leu Lys Arg Thr Glu
                965                 970                 975

Cys Gln Phe Leu Tyr Glu Val Arg Gly Glu Thr Tyr Leu Lys Gly Arg
                980                 985                 990

Gly Asn Glu Thr Thr Tyr Trp Leu Thr Gly Met Lys Asp Gln Lys Phe
            995                 1000                1005

Asn Leu Pro Thr Pro Pro Thr Val Glu Asn Gln Gln Arg Leu Gln Ala
    1010                1015                1020

Glu Phe Ser Asp Met Ile Ala Asn Ser Leu Gln Lys Arg Gln Ala Ala
1025                1030                1035                1040

Gly Ile Arg Ser Gln Lys Pro Arg Arg Val Ala Ser Tyr Lys Lys Gly
                1045                1050                1055

Thr Leu Glu Tyr Leu Gln Leu Asn Thr Thr Asp Lys Glu Ser Thr Tyr
            1060                1065                1070

Phe
```

METASTATIC COLORECTAL CANCER VACCINE

FIELD OF THE INVENTION

The invention relates to prophylactic and therapeutic vaccines for protecting individuals against metastatic colorectal cancer and for treating individuals who are suffering from metastatic colorectal cancer.

BACKGROUND OF THE INVENTION

Colorectal cancer is the third most common neoplasm worldwide. The mortality rate of newly diagnosed large bowel cancer approaches 50% and there has been little improvement over the past 40 years. Most of this mortality reflects local, regional and distant metastases.

Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recrudescence.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. Similarly, diagnosis of metastatic or recurrent disease earlier potentially carries with it a better prognosis.

Recent discoveries have shown that mutations of the human APC (Adenomatous Polyposis Coli) gene are responsible for both sporadic and familial colorectal cancers. Germline mutations of APC are found in inherited familial cancers such as Gardner's syndrome, attenuated adenomatous polyposis coli, heredity flat adenoma syndrome and familial adenomatous polyposis (FAP). FAP is an autosomal dominant inherited disease predisposing the patient to colon cancer. Patients inheriting a single mutant allele of APC develop hundreds to thousands of adenomatous polyps in the second to third decades of life, which if left untreated progress to malignant carcinomas. Genetic linkage analysis localized the APC gene to human chromosome 5q21-q22, a region frequently associated with allelic loss of the wildtype 5q allele. Mutations in APC are also implicated in sporadic colorectal cancers and in extracolonic tumors, such as gastric and small intestinal polyps, osteomas, sarcomas and desmoidal tumors.

There is a need for improved methods of treating individuals suffering from metastasized colon cancer. There is a need for compositions useful to treat individuals suffering from metastasized colon cancer. There is a need for improved methods of preventing a recurrence of metastasized colon cancer in individuals who have been treated for metastasized colon cancer. There is a need for compositions useful to prevent a recurrence of metastasized colon cancer in individuals who have been treated for metastasized colon cancer. There is a need for improved methods of preventing metastasized colon cancer in individuals, particularly those who have been identified as having a genetic predisposition for colon cancer. There is a need for compositions useful for preventing metastasized colon cancer in individuals.

SUMMARY OF THE INVENTION

The invention relates to an isolated protein comprising at least one epitope of human ST receptor protein. In some embodiments, the epitope is an epitope of the extracellular domain of the human ST receptor protein. In some embodiments, the epitope is an epitope of the transmembrane domain of the human ST receptor protein. In some embodiments, the epitope is an epitope of the cytoplasmic domain of the human ST receptor protein. In some embodiments, the isolated protein comprises the extracellular domain of the human ST receptor protein. In some embodiments, the isolated protein comprises the transmembrane domain of the human ST receptor protein. In some embodiments, the isolated protein comprises the cytoplasmic domain of the human ST receptor protein. In some embodiments, the isolated protein comprises the human ST receptor protein. In some embodiments, the isolated protein consists of the human ST receptor protein.

The invention relates to vaccines which comprise such proteins and a pharmaceutically acceptable carrier or diluent.

The invention relates to a haptenized protein comprising at least one epitope of human ST receptor protein. In some embodiments, the epitope is an epitope of the extracellular domain of the human ST receptor protein. In some embodiments, the epitope is an epitope of the transmembrane domain of the human ST receptor protein. In some embodiments, the epitope is an epitope of the cytoplasmic domain of the human ST receptor protein. In some embodiments, the haptenized protein comprises the extracellular domain of the human ST receptor protein. In some embodiments, the haptenized protein comprises the transmembrane domain of the human ST receptor protein. In some embodiments, the haptenized protein comprises the cytoplasmic domain of the human ST receptor protein. In some embodiments, the haptenized protein comprises the human ST receptor protein. In some embodiments, the haptenized protein consists of the human ST receptor protein.

The invention relates to vaccines which comprise such haptenized proteins and a pharmaceutically acceptable carrier or diluent.

The invention relates to nucleic acid molecules that encode a protein comprising at least one epitope of human ST receptor protein. In some embodiments, the nucleic acid molecule encodes a protein with an epitope of the extracellular domain of the human ST receptor protein. In some embodiments, the nucleic acid molecule encodes a protein with an epitope of the transmembrane domain of the human ST receptor protein. In some embodiments, the nucleic acid molecule encodes a protein with an epitope of the cytoplasmic domain of the human ST receptor protein. In some embodiments, the nucleic acid molecule encodes a protein that protein comprises the extracellular domain of the human ST receptor protein. In some embodiments, the nucleic acid molecule encodes a protein that comprises the transmembrane domain of the human ST receptor protein. In some embodiments, the nucleic acid molecule encodes a protein that comprises the cytoplasmic domain of the human ST receptor protein. In some embodiments, the nucleic acid molecule encodes a protein that comprises the human ST receptor protein. In some embodiments, the nucleic acid molecule encodes human ST receptor protein. In some embodiments, the nucleic acid molecule is a plasmid.

The invention relates to vaccines which comprise such nucleic acid molecules and a pharmaceutically acceptable carrier or diluent.

The invention relates to vectors that comprise nucleic acid molecules that encode a protein comprising at least one epitope of human ST receptor protein. In some embodiments, the vector comprises a nucleic acid molecule that encodes a protein with an epitope of the extracellular domain of the human ST receptor protein. In some embodiments, the vector comprises a nucleic acid molecule that encodes a protein with an epitope of the transmembrane domain of the human ST receptor protein. In some embodiments, the vector comprises a nucleic acid molecule that encodes a protein with an epitope of the cytoplasmic domain of the human ST receptor protein. In some embodiments, the vector comprises a nucleic acid molecule that encodes a protein that protein comprises the extracellular domain of the human ST receptor protein. In some embodiments, the vector comprises a nucleic acid molecule that encodes a protein that comprises the transmembrane domain of the human ST receptor protein. In some embodiments, the vector comprises a nucleic acid molecule that encodes a protein that comprises the cytoplasmic domain of the human ST receptor protein. In some embodiments, the vector comprises a nucleic acid molecule that encodes a protein that comprises the human ST receptor protein. In some embodiments, the vector comprises a nucleic acid molecule that encodes human ST receptor protein. In some embodiments, the vector is a virus or a bacterial cell. In some embodiments, the vector is a recombinant vaccinia virus.

The invention relates to vaccines which comprise such vectors and a pharmaceutically acceptable carrier or diluent.

The invention relates to killed or inactivated cells or particles that comprise a protein comprising at least one epitope of human ST receptor protein. In some embodiments, the killed or inactivated cells or particles comprise a protein with an epitope of the extracellular domain of the human ST receptor protein. In some embodiments, the killed or inactivated cells or particles comprise a protein with an epitope of the transmembrane domain of the human ST receptor protein. In some embodiments, the killed or inactivated cells or particles comprise a protein with an epitope of the cytoplasmic domain of the human ST receptor protein. In some embodiments, the killed or inactivated cells or particles comprise the extracellular domain of the human ST receptor protein. In some embodiments, the killed or inactivated cells or particles vector comprise the transmembrane domain of the human ST receptor protein. In some embodiments, the killed or inactivated cells or particles comprise the cytoplasmic domain of the human ST receptor protein. In some embodiments, the killed or inactivated cells or particles comprise the human ST receptor protein. In some embodiments, the killed or inactivated cells or particles vector is a killed or inactivated colorectal tumor cells.

The invention relates to vaccines which comprise such killed or inactivated cells or particles and a pharmaceutically acceptable carrier or diluent.

The invention relates to haptenized killed or inactivated cells or particles that comprise a protein comprising at least one epitope of human ST receptor protein. In some embodiments, the haptenized killed or inactivated cells or particles comprise a protein with an epitope of the extracellular domain of the human ST receptor protein. In some embodiments, the haptenized killed or inactivated cells or particles comprise a protein with an epitope of the transmembrane domain of the human ST receptor protein. In some embodiments, the haptenized killed or inactivated cells or particles comprise a protein with an epitope of the cytoplasmic domain of the human ST receptor protein. In some embodiments, the haptenized killed or inactivated cells or particles comprise the extracellular domain of the human ST receptor protein. In some embodiments, the haptenized killed or inactivated cells or particles vector comprise the transmembrane domain of the human ST receptor protein. In some embodiments, the haptenized killed or inactivated cells or particles comprise the cytoplasmic domain of the human ST receptor protein. In some embodiments, the haptenized killed or inactivated cells or particles comprise the human ST receptor protein. In some embodiments, the haptenized killed or inactivated cells or particles vector is a killed or inactivated colorectal tumor cells.

The invention relates to vaccines which comprise such haptenized killed or inactivated cells or particles and a pharmaceutically acceptable carrier or diluent.

The present invention relates to methods of treating individuals suffering from metastasized colorectal cancer. The method of the present invention provides administering to such an individual a therapeutically effective amount of a vaccine of the invention. The invention relates to the use of such vaccines as immunotherapeutics.

The present invention relates to methods of treating individuals susceptible metastasized colorectal cancer. The method of the present invention provides administering to such an individual an amount of a vaccine of the invention effective to prevent or combat metastasized colorectal cancer. The present invention relates to the use of the vaccines of the invention prophylactically.

DETAILED DESCRIPTION OF THE INVENTION

U.S. Ser. No. 08/141,892 filed on Oct. 26, 1993 (which is scheduled to issue on May 21, 1996 as U.S. Pat. No. 5,518,888), U.S. Ser. No. 08/305,056 filed on Sep. 13, 1994, and PCT Application Serial Number PCT/US94/12232 filed Oct. 26, 1994, which are each incorporated herein by reference, describe compositions for and methods of treating, imaging and detecting metastasized colon cancer.

As used herein, the terms "ST receptor" and "guanylin cyclase C" are interchangeable and meant to refer to the receptors found on colorectal cells, including local and metastasized colorectal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain ST receptors and are therefore amenable to the methods of the present invention using the compounds of the present invention.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to metastasized colorectal cancer cells.

As used herein, the term "metastasized colorectal cancer cells" is meant to refer to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, "an individual is suspected of being susceptible to metastasized colorectal cancer" is meant to refer to an individual who is at an above-average risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence. Other factors which may contribute to an above-average risk of developing metastasized colorectal cancer which would thereby lead to the classification of an individual as being suspected of being susceptible to metastasized colorectal cancer may be based upon an individual's specific genetic, medical and/or behavioral background and characteristics.

Heat stable toxin ST, which is produced by *E. coli*, as well as other organisms, is responsible for endemic diarrhea in developing countries and travelers diarrhea. ST induces intestinal secretion by binding to specific receptors, ST receptors, in the apical brush border membranes of the mucosal cells lining the intestinal tract. Binding of ST to ST receptors is non-covalent and occurs in a concentration-dependent and saturable fashion. Once bound, ST-ST receptor complexes appear to be internalized by intestinal cells, i.e. transported from the surface into the interior of the cell. Binding of ST to ST receptors triggers a cascade of biochemical reactions in the apical membrane of these cells resulting in the production of a signal which induces intestinal cells to secrete fluids and electrolytes, resulting in diarrhea.

ST receptors are unique in that they are only localized in the apical brush border membranes of the cells lining the intestinal tract. Indeed, they are not found in any other cell type in placental mammals. In addition, ST receptors are almost exclusively localized to the apical membranes, with little being found in the basolateral membranes on the sides of intestinal cells.

Mucosal cells lining the intestine are joined together by tight junctions which form a barrier against the passage of intestinal contents into the blood stream and components of the blood stream into the intestinal lumen. Therefore, the apical location of ST receptors isolates these receptors from the circulatory system so that they may be considered to exist separate from the rest of the body; essentially the "outside" of the body. Therefore, the rest of the body is considered "outside" the intestinal tract, i.e. extraintestinal. Compositions administered "outside" the intestinal tract are maintained apart and segregated from the only cells which normally express ST receptors. Conversely, tissue samples taken from tissue outside of the intestinal tract, i.e. extraintestinal tissue samples, do not normally contain cells which express ST receptors.

In individuals suffering from colorectal cancer, the cancer cells are often derived from cells that produce and display the ST receptor and these cancer cells continue to produce and display the ST receptor on their cell surfaces. Indeed, T84 cells, which are human colonic adenocarcinoma cells isolated from lung metastases, express ST receptors on their cell surface. Similarly, HT29glu-cells, which are human colonic adenocarcinoma cells, express receptors for ST. Thus, in individuals suffering from colorectal cancer, some metastasized intestinal cancer cells express ST receptors.

An effort was undertaken to determine the proportion of colorectal tumors which have the ST receptor. Each of the tumors tested were independently confirmed to be colorectal cancer by standard techniques of surgical pathology. Every one of the colorectal cancer tumors tested, including local colorectal tumors and metastasized colorectal tumors (liver, lung, lymph node, peritoneum, ovary) possessed ST receptors. In each case, the affinity and density of receptors was amenable for targeting. Normal liver, lymph node, peritoneum, gall bladder, ovary, stomach, kidney and lung cells were found not to possess ST receptors.

When such cancer cells metastasize, the metastasized cancer cells continue to produce and display the ST receptor. The expression of ST receptors on the surfaces of metastatic tumors provides a target which can be used to distinguish the metastasized colorectal cancer cells from normal extraintestinal cells. This target is useful in the detection, imaging and treatment of metastasized colorectal cancer.

According to the present invention, the ST receptor protein serves as a target against which a protective and therapeutic immune response can be induced. Specifically, vaccines are provided which induce an immune response against the ST receptor protein. The vaccines of the invention include, but are not limited to, the following vaccine technologies:

1) DNA vaccines, i.e. vaccines in which DNA that encodes at least an epitope from ST receptor protein is administered to an individual's cells where the epitope is expressed and serves as a target for an immune response;

2) infectious vector mediated vaccines such as recombinant adenovirus, vaccinia, Salmonella, and BCG wherein the vector carries genetic information that encodes at least an epitope of ST receptor protein such that when the infectious vector is administered to an individual, the epitope is expressed and serves as a target for an immune response;

3) killed or inactivated vaccines which a) comprise either killed cells or inactivated viral particles that display at least an epitope of the ST receptor protein and b) when administered to an individual serves as a target for an immune response;

3) haptenized killed or inactivated vaccines which a) comprise either killed cells or inactivated viral particles that display at least an epitope of the ST receptor, b) are haptenized to be more immunogenic and c) when administered to an individual serves as a target for an immune response;

4) subunit vaccines which are vaccines that include protein molecules that include at least an epitope the ST receptor protein; and 5) haptenized subunit vaccines which are vaccines that a) include protein molecules that include at least an epitope the ST receptor protein and b) are haptenized to be more immunogenic.

The present invention relates to administering to an individual a protein or nucleic acid molecule that comprises or encodes, respectively, an immunogenic epitope against which an therapeutic and prophylactic immune response can be induced. Such epitopes are generally at least 6-8 amino acids in length. The vaccines of the invention therefore comprise proteins which are at least, or nucleic acids which encode at least, 6-8 amino acids in length from ST receptor protein. The vaccines of the invention may comprise proteins which are at least, or nucleic acids which encode at least, the entire ST receptor protein. The vaccines of the invention may comprise proteins which are at least, or nucleic acids which encode at least 10 to about 1000 amino acids in length from ST receptor protein. The vaccines of the invention may comprise proteins which are at least, or nucleic acids which encode at least, about 25 to about 500 amino acids in length from ST receptor protein. The vaccines of the invention may comprise proteins which are at least, or nucleic acids which encode at least, about. 50 to about 400 amino acids in length from ST receptor protein. The vaccines of the invention may comprise proteins which are at least, or nucleic acids which encode at least, about 100 to about 300 amino acids in length from ST receptor protein. In preferred embodiments, fragments of ST receptor protein that include the extracellular domain are provided.

The present invention relates to compositions for and methods of treating individuals who are known to have metastasized colorectal cancer. Metastasized colorectal cancer may be diagnosed by those having ordinary skill in the art using art accepted clinical and laboratory pathology protocols and/or those described in U.S. Ser. No. 08/141,892 filed on Oct. 26, 1993, U.S. Ser. No. 08/305,056 filed on Sep. 13, 1994, and PCT Application Serial Number PCT/US94/12232 filed Oct. 26, 1994. The present invention provides an immunotherapeutic vaccine useful to treat individuals who have been diagnosed as suffering from metastasized colorectal cancer. The immunotherapeutic vaccines of the present invention may be administered in combination with other therapies including, but not limited to those described in U.S. Ser. No. 08/141,892 filed on Oct. 26, 1993, U.S. Ser. No. 08/305,056 filed on Sep. 13, 1994, and PCT Application Serial Number PCT/US94/12232 filed Oct. 26, 1994.

The present invention relates to compositions for and methods of preventing metastatic colorectal cancer in individual is suspected of being susceptible to metastasized colorectal cancer. Such individuals include those whose family medical history indicates above average incidence of colorectal cancer among family members and/or those who have already developed colorectal cancer and have been effectively treated who therefore face a risk of relapse and recurrence. Such individuals include those which have been diagnosed as having colorectal cancer including localized only or localized and metastasized colorectal cancer which has been resected or otherwise treated. Such individuals also include those with an elevated risk as ascertained by genetic evaluation. For example, individuals with APC mutations can be identified following the U.S. Pat. No. 5,352,775 issued Oct. 4, 1992 to Albertsen et al., which is incorporated herein by reference. Furthermore, such individuals include: those suffering from inflammatory bowel disease, particularly those with ulcerative colitis; those with colonic polyps; those with familial adenomatous polyposis, a heritable mutation predisposing patients to develop large numbers of intestinal polyps; those with Peutz-Jeghers syndrome; those with hereditary nonpolyposis coli, a heritable mutation which predisposes people to develop colon carcinoma; those with Turcot syndrome-colon carcinoma in conjunction with independent tumors of the central nervous system; and individuals engaging in rectal intercourse. The vaccines of the present invention may be to susceptible individuals prophylactically to prevent and combat colorectal cancer metastasis.

The invention relates to compositions which are the active components of such vaccines or required to make the active components, to methods of making such compositions including the active components, and to methods of making and using vaccines.

The nucleotide sequence that encodes human ST receptor protein is disclosed as SEQ ID NO:1. The amino acid sequence of human ST receptor is also disclosed in SEQ ID NO:1. Generally, the extracellular domain refers to the amino acids about 24 to about 454. The transmembrane region refers to amino acids about 455 to about 475. The cytoplasmic domain refers to amino acids about 476 to about 1093.

Accordingly, some aspects of the invention relate to isolated proteins that comprise at least one ST receptor epitope. The epitope may be from the ST receptor extracellular domain, transmembrane domain or cytoplasmic domain. In preferred embodiments, the protein comprises at least one epitope from the extracellular domain. The protein may comprise ST receptor protein sequences or consist of ST receptor protein sequences. The protein may comprise the entire ST receptor protein, consist of the entire ST receptor protein, comprise a fragment of the ST receptor protein, or consist of a fragment of the ST receptor protein. In some preferred embodiments, the protein is a soluble form of the extracellular domain. In some preferred embodiments, the protein is a soluble form of the extracellular domain with a portion of the transmembrane domain.

Some aspects of the invention relate to the above described isolated proteins which are haptenized to render them more immunogenic. That is, some aspects of the invention relate to haptenized proteins that comprise at least one ST receptor epitope. The epitope may be from the ST receptor extracellular domain, transmembrane domain or cytoplasmic domain. The protein may comprise ST receptor protein sequences or consist of ST receptor protein sequences. The protein may comprise the entire ST receptor protein, consist of the entire ST receptor protein, comprise a fragment of the ST receptor protein, or consist of a fragment of the ST receptor protein. In some preferred embodiments, the haptenized protein comprises a soluble form of the extracellular domain. In some preferred embodiments, the haptenized protein is a soluble form of the extracellular domain with a portion of the transmembrane domain.

Some aspects of the invention nucleic acid molecules that encode the above described isolated proteins.

Accordingly, some aspects of the invention relate to isolated nucleic acid molecules that encode proteins that comprise at least one ST receptor epitope. The epitope may be from the ST receptor extracellular domain, transmembrane domain or cytoplasmic domain. In preferred embodiments, the isolated nucleic acid molecules encodes a protein that comprises at least one epitope from the extracellular domain. The isolated nucleic acid molecule may encode a protein that comprises or consists of ST receptor protein sequences. The isolated nucleic acid molecule may encode a protein that comprises or consists of the entire ST receptor protein, or a protein that comprises or consists of a fragment of the ST receptor protein. In some embodiments, the isolated nucleic acid molecule encodes non-ST receptor protein sequences which are useful to render the ST receptor protein sequences more immunogenic.

Naked DNA vaccines are described in PCT/US90/01515, which is incorporated herein by reference. Others teach the use of liposome mediated DNA transfer, DNA delivery using microprojectiles (U.S. Pat. No. 4,945,050 issued Jul. 31, 1990 to Sanford et al., which is incorporated herein by reference), and DNA delivery using electroporation. In each case, the DNA may be plasmid DNA that is produced in bacteria, isolated and administered to the animal to be treated. The plasmid DNA molecules are taken up by the cells of the animal where the sequences that encode the protein of interest are expressed. The protein thus produced provides a therapeutic or prophylactic effect on the animal.

The use of vectors including viral vectors and other means of delivering nucleic acid molecules to cells of an individual in order to produce a therapeutic and/or prophylactic immunological effect on the individual are similarly well known. Recombinant vaccines that employ vaccinia vectors are, for example, disclosed in U.S. Pat. No. 5,017,487 issued May 21, 1991 to Stunnenberg et al. which is incorporated herein by reference.

In some cases, tumor cells from the patient are killed or inactivated and administered as a vaccine product. Berd et al. May 1986 *Cancer Research* 46:2572-2577 and Berd et al. May 1991 *Cancer Research* 51:2731-2734, which are incorporated herein by reference, describes the preparation and use of tumor cell based vaccine products. According to some aspects of the present invention, the methods and techniques described in Berd et al. are adapted by using colorectal cancer cells instead of melanoma cells.

The manufacture and use of subunit vaccines are well known. One having ordinary skill in the art can isolate the nucleic acid molecule that encode ST receptor protein or a fragment thereof or a protein that comprises the ST receptor protein or a fragment thereof. Once isolated, the nucleic acid molecule can be inserted it into an expression vector using standard techniques and readily available starting materials. Rudner et al. May 1995 *Proc. Natl. Acad. Sci. USA* 92:5169-5173 disclosed the cloning and expression of the extracellular domain of human ST receptor and purification of the same using a Flag immunoaffinity epitope and antibody therefor.

The recombinant expression vector that comprises a nucleotide sequence that encodes the nucleic acid molecule that encode ST receptor protein or a fragment thereof or a protein that comprises the ST receptor protein or a fragment thereof. As used herein, the term "recombinant expression vector" is meant to refer to a plasmid, phage, viral particle or other vector which, when introduced into an appropriate host, contains the necessary genetic elements to direct expression of the coding sequence that encodes the protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors of the invention are useful for transforming hosts to prepare recombinant expression systems for preparing the isolated proteins of the invention.

The present invention relates to a host cell that comprises the recombinant expression vector that includes a nucleotide sequence that encodes the ST receptor protein or a fragment thereof or a protein that comprises the ST receptor protein or a fragment thereof. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the proteins of the invention. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes the ST receptor protein or a fragment thereof or a protein that comprises the ST receptor protein or a fragment thereof operably linked to a mammary cell specific promoter whereby the coding sequence is only expressed in mammary cells and the recombinant protein so expressed is recovered from the animal's milk.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce the ST receptor protein or a fragment thereof or a protein that comprises the ST receptor protein or a fragment thereof using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes the ST receptor protein or a fragment thereof or a protein that comprises the ST receptor protein or a fragment thereof is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, the ST receptor protein or a fragment thereof or a protein that comprises the ST receptor protein or a fragment thereof that is produced using such expression systems. The methods of purifying the ST receptor protein or a fragment thereof or a protein that comprises the ST receptor protein or a fragment thereof using antibodies which specifically bind to the protein are well known. Antibodies which specifically bind to a particular protein may be used to purify the protein from natural sources using well known techniques and readily available starting materials. Such antibodies may also be used to purify the protein from material present when producing the protein by recombinant DNA methodology. The present invention relates to antibodies that bind to an epitope which is present on the ST receptor protein or a fragment thereof or a protein that comprises the ST receptor protein or a fragment thereof. As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. Antibodies that bind to an epitope which is present on the ST receptor protein or a fragment thereof or a protein that comprises the ST receptor protein or a fragment thereof are useful to isolate and purify the protein from both natural sources or recombinant expression systems using well known techniques such as affinity chromatography. Immunoaffinity techniques generally are described in Waldman et al. 1991 *Methods of Enzymol.* 195:391-396, which is incorporated herein by reference. Antibodies are useful to detect the presence of such protein in a sample and to determine if cells are expressing the protein. The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, the ST receptor protein or a fragment thereof or a protein that comprises the ST receptor protein or a fragment thereof, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the ST receptor protein or a fragment thereof or a protein that comprises the ST receptor protein or a fragment thereof, the hybridoma which produces them is cultured to produce a continuous supply of antibodies.

In some embodiments of the invention, transgenic non-human animals are generated. The transgenic animals according to the invention contain nucleotides that encode the ST receptor protein or a fragment thereof or a protein that comprises the ST receptor protein or a fragment thereof under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the ST receptor protein or a fragment thereof or a protein that comprises the ST receptor protein or a fragment thereof. Preferred animals are goats and rodents, particularly rats and mice.

In addition to producing these proteins by recombinant techniques, automated peptide synthesizers may also be employed to produce the ST receptor protein or a fragment thereof or a protein that comprises the ST receptor protein or a fragment thereof of the invention. Such techniques are well known to those having ordinary skill in the art and are useful if derivatives which have substitutions not provided for in DNA-encoded protein production.

In some embodiments, the protein that makes up a subunit vaccine or the cells or particles of a killed or inactivated vaccine may be haptenized to increase immunogenicity. In some cases, the haptenization is the conjugation of a larger molecular structure to the ST receptor protein or a fragment thereof or a protein that comprises the ST receptor protein or a fragment thereof. In some cases, tumor cells from the patient are killed and haptenized as a means to make an effective vaccine product. In cases in which other cells, such as bacteria or eukaryotic cells which are provided with the genetic information to make and display the ST receptor protein or a fragment thereof or a protein that comprises the ST receptor protein or a fragment thereof, are killed and used as the active vaccine component, such cells are haptenized to increase immunogenicity. Haptenization is well known and can be readily performed.

Methods of haptenizing cells generally and tumor cells in particular are described in Berd et al. May 1986 *Cancer Research* 46:2572-2577 and Berd et al. May 1991 *Cancer Research* 51:2731-2734, which are incorporated herein by reference. Additional haptenization protocols are disclosed in Miller et al. 1976 *J. Immunol.* 117(5:1):1591-1526.

Haptenization compositions and methods which may be adapted to be used to prepare haptenized ST immunogens according to the present invention include those described in the following U.S. Patents which are each incorporated herein by reference: U.S. Pat. No. 5,037,645 issued Aug. 6, 1991 to Strahilevitz; U.S. Pat. No. 5,112,606 issued May 12, 1992 to Shiosaka et al.; U.S. Pat. No. 4,526716 issued Jul. 2, 1985 to Stevens; U.S. Pat. No. 4,329,281 issued May 11, 1982 to Christenson et al.; and U.S. Pat. No. 4,022,878 issued May 10, 1977 to Gross. Peptide vaccines and methods of enhancing immunogenicity of peptides which may be adapted to modify ST immunogens of the invention are also described in Francis et al. 1989 *Methods of Enzymol.* 178:659-676, which is incorporated herein by reference. Sad et al. 1992 *Immunolology* 76:599-603, which is incorporated herein by reference, teaches methods of making immunotherapeutic vaccines by conjugating gonadotropin releasing hormone to diphtheria toxoid. ST immunogens may be similarly conjugated to produce an immunotherapeutic vaccine of the present invention. MacLean et al. 1993 *Cancer Immunol. Immunother.* 36:215-22.2, which is incorporated herein by reference, describes conjugation methodologies for producing immunotherapeutic vaccines which may be adaptable to produce an immunotherapeutic vaccine of the present invention. The hapten is keyhole limpet hemocyanin which may be conjugated to an ST immunogen.

As used herein, the term "ST receptor immunogen" is meant to refer to the ST receptor protein or a fragment thereof or a protein that comprises the ST receptor protein or a fragment thereof, haptenized ST receptor protein or a haptenized fragment thereof or a haptenized protein that comprises the ST receptor protein or a haptenized fragment thereof, cells and particles which display at least one ST receptor epitope, and haptenized cells and haptenized particles which display at least one ST receptor epitope Vaccines according to some aspects of the invention comprise a pharmaceutically acceptable carrier in combination with an ST receptor immunogen. Pharmaceutical formulations are well known and pharmaceutical compositions comprising such proteins may be routinely formulated by one having ordinary skill in the art. Suitable pharmaceutical carriers are described in *Remington's Pharmaceutical Sciences*, A. Osol, a standard reference text in this field, which is incorporated herein by reference. The present invention relates to an injectable pharmaceutical composition that comprises a pharmaceutically acceptable carrier and an ST receptor immunogen. The ST receptor immunogen is preferably sterile and combined with a sterile pharmaceutical carrier.

In some embodiments, for example, the ST receptor immunogen can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise the ST receptor immunogen in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

The vaccines of the present invention may be administered by any means that enables the immunogenic agent to be presented to the body's immune system for recognition and induction of an immunogenic response. Pharmaceutical compositions may be administered parenterally, i.e., intravenous, subcutaneous, intramuscular.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by routine methods.

---

The invention claimed is:

1. A method of treating an individual who has metastasized colorectal cancer comprising the step of administering to such an individual a therapeutically effective amount of an expression vector comprising a nucleic acid molecule that encodes SEQ ID NO:2 or a fragment thereof comprising amino acids 24-454 of SEQ ID NO:2.

2. A method of treating an individual who has been identified as being susceptible to metastasized colorectal cancer comprising the step of administering to such an individual a prophylactically effective amount of an expression vector comprising a nucleic acid molecule that encodes SEQ ID NO:2 or a fragment thereof comprising amino acids 24-454 of SEQ ID NO:2.

3. The method of claim 2 wherein the individual has been previously been diagnosed with colorectal cancer.

4. The method of claim 1 wherein said nucleic acid molecule encodes a protein that comprises SEQ ID NO:2.

5. The method of claim 1 wherein said nucleic acid molecule encodes a protein that comprises amino acids 24-454 of SEQ ID NO:2.

6. The method of claim 1 wherein said nucleic acid molecule encodes a protein that comprises amino acids 24-475 of SEQ ID NO:2.

7. The method of claim 2 wherein said nucleic acid molecule encodes a protein that comprises SEQ ID NO:2.

8. The method of claim 2 wherein said nucleic acid molecule encodes a protein that comprises amino acids 24-454 of SEQ ID NO:2.

9. The method of claim 2 wherein said nucleic acid molecule encodes a protein that comprises amino acids 24-475 of SEQ ID NO:2.

* * * * *

UNITED STATES PATENT AND TRADEMARK OFFICE
CERTIFICATE OF CORRECTION

PATENT NO.       : 7,598,229 B2                                        Page 1 of 1
APPLICATION NO. : 10/695578
DATED            : October 6, 2009
INVENTOR(S)      : Scott A. Waldman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 702 days.

Signed and Sealed this

Twenty-eighth Day of September, 2010

David J. Kappos
*Director of the United States Patent and Trademark Office*